United States Patent [19]

Crish et al.

[11] Patent Number: 4,608,985

[45] Date of Patent: Sep. 2, 1986

[54] ANTIDROMIC PULSE GENERATING WAVE FORM FOR COLLISION BLOCKING

[75] Inventors: Timothy J. Crish, North Olmsted; James D. Sweeney; J. Thomas Mortimer, both of Cleveland Heights, all of Ohio

[73] Assignee: Case Western Reserve University, Cleveland, Ohio

[21] Appl. No.: 659,825

[22] Filed: Oct. 11, 1984

[51] Int. Cl.⁴ .............................................. A61N 1/36
[52] U.S. Cl. .................................................. 128/419 R
[58] Field of Search ............... 128/419 R, 419 C, 642, 128/784–785, 802, 421–423

[56] References Cited

U.S. PATENT DOCUMENTS

| | | | |
|---|---|---|---|
| Re. 26,810 | 3/1970 | Schwartz et al. | 128/784 |
| 3,157,181 | 11/1964 | McCarty | 128/784 |
| 3,654,933 | 4/1972 | Hagfors | 128/784 |
| 3,738,368 | 6/1973 | Avery et al. | 128/784 |
| 3,774,618 | 11/1973 | Avery | 128/784 |
| 3,911,930 | 10/1975 | Hagfors et al. | 128/421 |
| 4,019,519 | 4/1977 | Geerling | 128/422 |
| 4,294,245 | 10/1981 | Bussey | 128/421 |
| 4,341,221 | 7/1982 | Testerman | 128/642 |
| 4,515,168 | 5/1985 | Chester et al. | 128/421 |

OTHER PUBLICATIONS

"A Technique for Collision Block of Peripheral Nerve: Single Stimulus Analysis", IEEE Trans. on Biomed. Eng., vol. BME-28, No. 5, May 1981.
"A Technique for Collision Block of Peripheral Nerve: Frequency Dependence", IEEE Trans. on Biomed. Engr., vol. BME-28, No. 5, May 1981.
"Generation of Unidirectionally Propagated Action Potentials in a Peripheral Nerve by Brief Stimuli", Science, vol. 206, pp. 1311-1312, Dec. 1979.

Primary Examiner—William E. Kamm
Assistant Examiner—Mitchell J. Shein
Attorney, Agent, or Firm—Fay, Sharpe, Fagan, Minnich & McKee

[57] ABSTRACT

An electrode cuff (B) including a dielectric sleeve (10) and an annular cathode electrode (20) is disposed around a nerve trunk (A). An anode electrode (22) is disposed in body fluids in electrical communication with the nerve trunk. The cathode electrode is disposed off center within the dielectric sleeve. The flow of electric current from the anode to the cathode has a much greater amplitude along the nerve in the direction extending along the nerve trunk toward the cathode from the end of the dielectric sleeve toward which the cathode electrode is closest. A signal generator (C) applies a pulse train across the anode and cathode electrodes. The pulse train includes a plurality of alternating first amplitude pulse portions (40) and opposite polarity pulse portions (42). Each first polarity pulse includes a sharp leading edge (50) which rises abruptly to a preset amplitude (52). A trailing edge (56) of each first pulse portion decays smoothly into a leading edge (60) of each opposite polarity pulse portion without a discontinuity therebetween. The opposite polarity pulse portion has an amplitude (62) which is smaller than the triggering amplitude and a duration which is longer than the first polarity pulse portion duration. The amplitude and duration of the first and opposite polarity pulse portions are selected such that the net charge transfer in each direction is substantially the same.

17 Claims, 4 Drawing Figures ary pulses.

ANTIDROMIC PULSE GENERATING WAVE FORM FOR COLLISION BLOCKING

BACKGROUND OF THE INVENTION

The present invention relates to the biomedical arts for introducing electrical signals on nerve trunks. The present invention finds particular application in introducing a string of artificially generated antidromic pulses on the nerve trunk for collision blocking orthodromic pulses moving in the opposite direction along the nerve trunk and will be described with particular reference thereto. It is to be appreciated, however, that the invention may have broader applications and may apply electrical signals on nerve trunks for other purposes.

Heretofore, various techniques have been used to block nerve pulses passing along a nerve trunk. A common blocking technique was the application of DC currents on the nerve trunk. However, it has been found that the application of DC currents can be expected to cause nerve damage.

To eliminate the DC current induced nerve damage, others have suggested using an oscillating current such that the induced electrical current flowed alternately in both directions along the nerve trunk. It has been found that the application of high frequency stimulation blocks the passage of nerve signals therethrough. However, it appears that high frequency stimulation may, in effect, be overdriving neuromuscular junctions and depleting the neurotransmitter at the terminal end. That is, rather than blocking the passage of nerve stimuli on the nerve fiber or axon, the high frequency stimulation techniques may be overworking the nerve terminal to the point of exhaustion causing a failure of proper functioning.

Yet another blocking technique utilized a three electrode cuff which included a dielectric sleeve having a passage through which the nerve trunk passes. Three annular electrodes were arranged within the sleeve. A cathode was positioned near the center of the passage and a pair of anodes were positioned to either side. A signal generator was connected with the electrodes to apply an electrical pulse train that induced antidromic pulses on the nerve trunk. Each pulse of the pulse train included a rapid rise to a preselected amplitude, a 100 to 3000 microsecond plateau, and an exponential decay back to zero. This pulse train induced artificially generated antidromic pulses on the nerve trunk which traveled unidirectionally in the opposite direction to the normal pulse flow. The artificially generated antidromic pulses collided with and blocked further propagation of natural orthodromic pulses moving in the other direction on the nerve trunk. However, the application of a series of pulses of common polarity, again has been found to cause damage to neural tissues.

To eliminate this nerve damage, others have suggested applying a low amplitude, relatively long duration rectangular wave pulse of opposite polarity between each pulse of the above-described pulse train. The opposite polarity of the rectangular wave pulse balanced the net charge flow caused by the primary pulse. However, it has been found that at an upper limiting frequency, the sudden polarity change still tends to depolarize the nerve cell and cause transmission in the wrong direction. This tendency to generate artificial orthodromic pulses, of course, was undesirable. For example, if the antidromic blocking pulses were utilized to block stray excitation pulses moving toward a paralyzed patient's spastically contracted sphincter muscle over which control had been lost, the stray orthodromic pulses would cause undesired activation of the muscles of micturition.

The present invention contemplates a new and improved method and apparatus for artificially generating antidromic pulses.

SUMMARY OF THE INVENTION

In accordance with the present invention, there is provided a system for selectively blocking orthodromic action potentials passing along a nerve trunk. The system includes an electrode cuff including a cathode disposed around the nerve trunk and a dielectric shield disposed encircling the electrode and the nerve trunk to both sides of the electrode. An anode is electrically associated with body tissue such that electrical current flows from the anode through the body tissue and nerve trunk to the cathode. A signal generator is operatively connected with the cathode and anode for cyclically generating electrical pulses. Each pulse cycle includes a first polarity pulse which rises abruptly to a first preselected amplitude, retains the amplitude for a preselected duration, and decays smoothly from the amplitude. Each cycle further includes an opposite polarity phase whose leading edge is a smooth continuation of the first polarity pulse decaying trailing edge. The opposite polarity pulse rises smoothly to a magnitude whose absolute value is less than the first polarity pulse magnitude and which is too low to trigger action potentials. The opposite polarity pulse is substantially longer than the first polarity pulse such that the charge flow during the first and opposite polarity pulse is opposite but generally equal.

One advantage of the present invention is that orthodromic action potentials are blocked without the nerve damage associated with DC blocking techniques.

Another advantage is that orthodromic pulses are blocked without overdriving nerve terminals or depleting the neurotransmitter as in high frequency blocking techniques.

Yet another advantage is that the generation of stray counterdirectional action potentials is eliminated.

Still further advantages of the present invention will become apparent to those of ordinary skill in the art upon reading and understanding the following detailed description of the preferred embodiments.

BRIEF DESCRIPTION OF THE DRAWINGS

The invention may take form in various parts and arrangements of parts and in various steps and arrangements of steps. The drawings are only for purposes of illustrating a preferred embodiment of the invention and it should not be construed as limiting it.

DETAILED DESCRIPTION OF THE PREFERRED EMBODIMENTS

Figure 1:
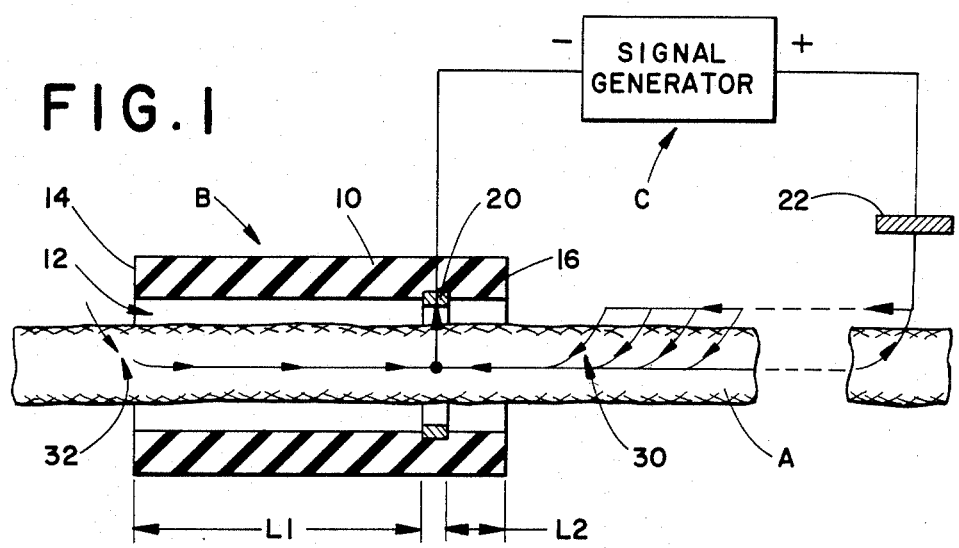
FIG. 1 is a diagrammatic illustration of an orthodromic nerve pulse blocking system, in partial section, in accordance with the present invention.

With particular reference to FIG. 1, a nerve trunk A extends through a central passage of an electrode cuff B. A signal generating means C applies the appropriate electrical potentials to body tissue, at least in part through the electrode cuff, for introducing a string of artificially generated antidromic pulses or other action potentials along the nerve trunk A.

The nerve trunk A includes a plurality of nerve fibers including an axis of axoplasm surrounded by regularly spaced myelin sheaths. The axon of each nerve cell under certain physiological conditions conducts electrical pulses from the dendrites and cell body or sense organs to the axon, i.e., orthodromic conduction. In response to an appropriate electric current, electrical action potentials traveling opposite the orthodromic pulses can be induced, i.e., antidromic pulses.

Figure 2:
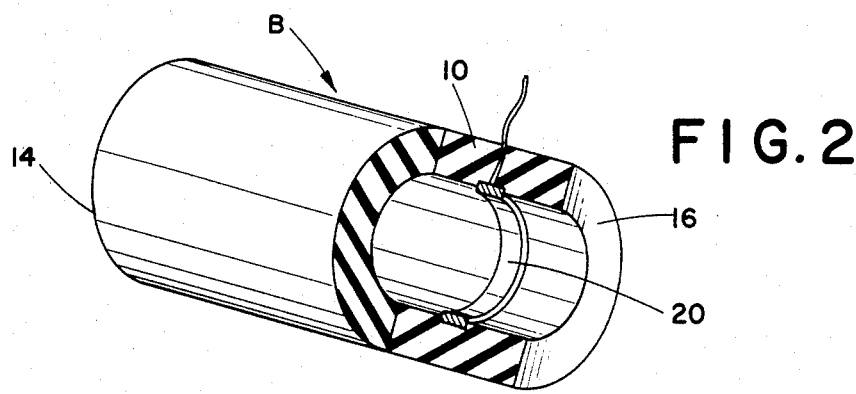
FIG. 2 is a perspective view of an asymmetric, single electrode cuff in accordance with the present invention.

With reference to FIGS. 1 and 2, the electrode cuff B includes an electrically non-conductive or dielectric sleeve 10 which defines an axial passage 12 therethrough. The dielectric sheath and axial passage extend from a first or escape end 14 disposed toward the origin of the orthodromic pulses to a second or arrest end 16. To receive the nerve trunk non-compressively, the central passage is about 30% or more larger in diameter than the nerve trunk. The gap between the nerve trunk and the cuff is filled by conductive body tissues and fluids after implantation. The axial passage 12 and the dielectric sheath are both circular in transverse cross section for simplicity of construction. However, it is contemplated that certain elliptical cross sections may also be suitable.

A single, annular electrode 20 is disposed in the axial passage. The electrode may be mounted on the inner surface of the dielectric sleeve within the axial passage provided that the electrode allows the nerve trunk A to pass uncompressed therethrough. Alternately, the electrode may be recessed into the dielectric sleeve such that its inner surface is flush with or below the dielectric passage. The electrode is positioned a length L1 from the escape end 14 and a length L2 from the arrest end 16. The electrode is disposed asymmetrically within the dielectric sleeve toward the escape end, i.e., length L1 is greater than length L2. More particularly, it has been found that excellent results are achieved with a 1 mm nerve trunk when the length L1 is between 1.7 and 7 times the length L2. Ratios greater than 7:1 also generate satisfactory antidromic pulses, but the electrode cuff is so long that its length tends to interfere with convenient implantation. Satisfactory results are achieved with the length L1 equal to 21 mm and the length L2 equal to 3 mm.

With continuing reference to FIG. 1, the signal generator C generates a pulse train which it applies between the cuff electrode 20 and a second electrode 22. The second electrode is disposed separately in the patient's body in an electrically conductive relationship to the nerve trunk A. Preferably, the second electrode is biased to function as an anode and is disposed to facilitate a first or hyperpolarizing current flow 30 from the anode 22, through the nerve trunk, to the cuff electrode 20.

Because the body fluids and tissues are electrically conductive, a second current 32 from the anode 22 also flows into the nerve trunk A upstream from the escape end 14 of the electrode cuff. The second current 32 flows along the nerve trunk in the opposite direction to the first current 30. If the second current 32 has a sufficiently high amplitude, it can cause the arrest of action potentials in the axons of the nerve trunk. However, the relative amplitude of the first and second currents varies in proportion to the asymmetry of the cuff electrode within the dielectric sleeve 10. That is, the more asymmetrically the cuff electrode 20 is positioned, i.e., the greater the ratio of the first length L1 to the second length L2, the greater the relative difference between the first and second currents. By placing the cuff electrode sufficiently asymmetrically, a unidirectional flow of antidromic pulses along the nerve trunk is generated flowing from the cathode 20 and beyond the escape end 14.

More specifically, the generation of unidirectional action potentials is commonly preceded by bidirectional propagation as the amplitude of the stimulus signal from the signal generator increases. If the stimulus signal amplitude increases beyond an appropriate unidirectional blocking amplitude, the secondary current also reaches the blocking amplitude and blocks the antidromic pulse propagation. Between the initial bidirectional action potential generation threshold and the bidirectional blocking threshold, a unidirectional block window is defined. Because the relative amplitudes of the first current 30 and the second current 32 vary with the asymmetry of the cathode electrode 20 within the cuff, the width of the unidirectional block window also varies with the electrode asymmetry. Further, the block window width varies with other factors which affect relative current flow such as the diameter of the axial passage 12, the length of the electrode cuff, and the like.

It will be appreciated that an analogous distribution of current flow in both directions in the nerve trunk can be obtained with an electrode cuff having a centrally disposed cathode and a pair of anodes, one to either side thereof. The signal generator is connected between the cathode and the anodes with an attenuator being disposed between the signal generator and the proximal end anode. By appropriately selecting the degree of signal attenuation, the relative amplitudes of the signals flowing in each direction through the nerve trunk is selectable in an analogous manner to the asymmetric positioning of the single electrode in the illustrated electrode cuff.

Figure 3:
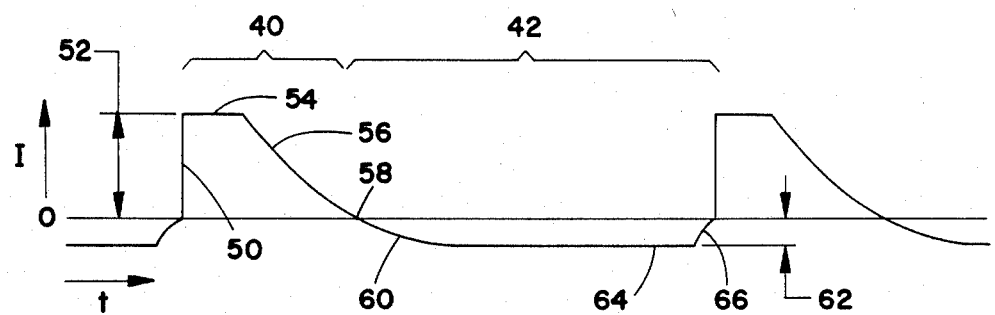
FIG. 3 is a current amplitude vs time graphic representation of an antidromic action potential generating wave form in accordance with the present invention; and, FIG. 4 is a schematic diagram of a biphasic regulated current generator for generating the wave form of FIG. 3.

With particular reference to FIG. 3, the signal generator C generates a series of regularly spaced, substantially identical current pulses. The stimulation signal may have a frequency of about 1 hertz up to 100 hertz or more. Each pulse cycle includes a first portion 40 having a first polarity or current direction and a second portion 42 having a second or opposite polarity or current direction. The first polarity portion 40 includes a leading edge 50 which rises rapidly to a preselected amplitude 52. Amplitudes of ¼ to 20 milliamps have been found to be satisfactory. As a specific example, a 24 mm electrode cuff with a 1.65 mm axial passage diameter, and an asymmetry of 7:1 achieved unidirectional blocking in a window between about ¼ and 1¾ milliamps. Each first polarity current pulse portion 40 further has a plateau phase or portion 54 which maintains the plateau amplitude for a preselected duration. The plateau phase 54 lasts about 1 to 10% of the cycle duration. After the preselected duration, the current amplitude decays exponentially along an exponential decay portion 56 reaching zero amplitude at a crossover point 58. Plateau amplitude durations of 100 to 3000 microseconds have been found to be satisfactory.

In the second pulse portion 42, the current changes polarity and increases in amplitude along an exponential current increase portion 60. At the interface or crossover point 58, the one polarity decay portion 56 and the opposite polarity increase portion 60 have a smooth, discontinuity free transition. Although the one polarity decay and the other polarity increase portions follow a common curve in the preferred embodiment, they may follow different smooth curves provided there is substantially no discontinuity along the combined decay and opposite polarity increase portions. The opposite polarity increase portion reaches a steady state amplitude 62 and holds the steady state amplitude for a steady state duration 64 almost until the beginning of the next cycle, substantially identical pulse. The opposite polarity wave form 64 quickly returns to zero amplitude along an edge 66 before the leading edge 50 of the next primary pulse occurs. The edge 66 is brief and may approach a sharp path.

The opposite polarity current amplitude 62 is sufficiently small that the reverse polarity current minimizes the possibility of inducing action potentials on the wave trunk. The magnitude of the opposite polarity amplitude 62 is selected such that the total current flow in the first and second portions of each cycle is equal but opposite. In this manner, there is no net charge transfer. It is to be appreciated that opposite polarity current pulses or portions of various shapes may be utilized provided the amplitude remains low and there are substantially no discontinuities along the path described by wave form portions 56 and 60.

With particular reference to FIG. 1 in operation, the electrode cuff B is surgically implanted around the nerve to be controlled. The signal generator is connected with the electrode cuff electrode 20 and the anode electrode 22. During the first polarity pulse portion of each cycle, the first or hyperpolarizing current 30 flows from the anode, through the tissue, and along the nerve trunk. The hyperpolarizing current increases adjacent the cuff, reaching a maximum current density adjacent the cathode 20. Current flows from the anode through body tissues and enters the axoplasm of the nerve between myelin sheath segments. The current hyperpolarizes the nerve at nodes of Ranvier near the ends of the electrode cuff. The first current exits, or depolarizes, the nerve at a node closely adjacent the cathode. The first current reaches a sufficient current density adjacent the cathode 20 that a pulse is generated on the nerve, one moving toward the escape end and one moving toward the arrest end. Each antidromic action potential leaves the escape end and travels along the nerve trunk therebeyond to collide with and annihilate an orthodromic pulse moving toward the cuff. The pulse generated at electrode 20 traveling in the orthodromic direction is arrested by the anodic current 30 at the arrest end 16.

More specifically, the wave form observed at the negative electrode or cathode 20 has the opposite sign to that shown in FIG. 3. In other words, it would appear negative when the figure appears positive. With reference to the nerve fibers adjacent electrode 20, the leading edge 50 of the wave form and the initial part of the plateau phase 54 cause action potentials to be generated on nerves in the vicinity of the electrode 20. The current flowing through this electrode 20 for the remaining portion of this phase of the cycle has little significance to the adjacent nerves. After action potential initiation, the effect of the remaining current of this phase is on the sites at the ends of the cuff.

The action potentials initiated under the electrode 20 will be propagated on each nerve fiber toward both ends of the cuff. Under proper operating conditions the antidromic pulse will leave the cuff at the escape end 14 and the orthodromic pulse will be stopped at the arrest end 16. The first current 30 flows through the nerve membrane in the opposite direction to that current flowing through the membrane under the electrode 20. The effect of current 30 is to counter the depolarizing current flow arising from the action potential propagating toward the arrest end 16, which was initiated during the initial phases of the leading edge 50 and plateau phase 54. The hyperpolarizing current 30 is maintained for a period that is long enough to counter the depolarizing currents naturally arising from the approaching action potential initiated in the vicinity of electrode 20. This period is the majority of the plateau phase and can extend into the decaying phase 56.

The hyperpolarizing current 30 flowing during the plateau and decay phases 54 and 56 not only opposes the depolarizing currents of the approaching action potential but hyperpolarizes the nerve membrane in the vicinity of the arrest end 16, which can leave the membrane in a hyperexcitable state. If the current were to be abruptly terminated at the completion of the plateau phase 54 the hyperpolarized membrane could spontaneously depolarize, producing an action potential that would be propagated past the arrest end 16 of the cuff.

The spontaneous generation of the action potential can be eliminated by gradually reducing the stimulus amplitude as shown in the decay phase 56 of the stimulus wave form. Gradually reducing the stimulus can eliminate the spontaneous generation of an action potential without eliminating the hyperexcitability state. If a discontinuity occurs in the wave form, such as an abrupt transition during the decaying phase of the stimulus, it may initiate an action potential in the hyperexcitable membrane. Because the membrane may still be in the hyperexcitable state, an action potential may be initiated even if a discontinuity occurs at the zero crossing point 58.

In order to avoid nerve injury due to the accumulation of the biproducts of the electrochemical reactions that occur during current passage through the electrode, a reverse current 42 is passed through the electrode between stimulus pulses. The reverse current magnitude 62 should be as low as possible and free of discontinuities to avoid depolarizing the membrane and initiating an action potential in the region of the hyperpolarizing current. It is desirable, but may not be absolutely necessary, that the charge passed during the positive and negative phases or portions 40,42 be equal. Therefore, it is important that the circuit used to generate this wave form be capable of automatically adjusting the magnitude 62 of the reverse phase 42 to accomodate changes in the positive phase 40 or the cycle length. Any tendency to initiate an action potential during the hyperexcitable stage can be reduced by making the transition between the positive phase 40 and the negative phase 42 free of any discontinuity.

It should be noticed that the second current 32 flows in the same direction through the nerve membrane as does the hyperpolarizing current 30, both being in a direction to hyperpolarize the membrane. Therefore it is possible for the second current 32 to be sufficiently large that it would block the antidromic pulse leaving the escape end 14. When this occurs there is bidirectional block of the action potentials initiated under electrode 20. The second current 32 is always less than the first current 30 because of the asymmetry of the electrode cuff. The magnitude of the current 52 at electrode 20 when the hyperpolarizing current 30 is sufficient to block the orthodromic pulse defines the onset of unidirectional pulse propagation. The magnitude of the current 52 at the electrode 20 when the second current 32 is sufficient to block the antidromic pulse defines the onset of bidirectional pulse arrest. The difference between these two current magnitudes, measured by electrode 20, defines the arrest or block window.

Figure 4:
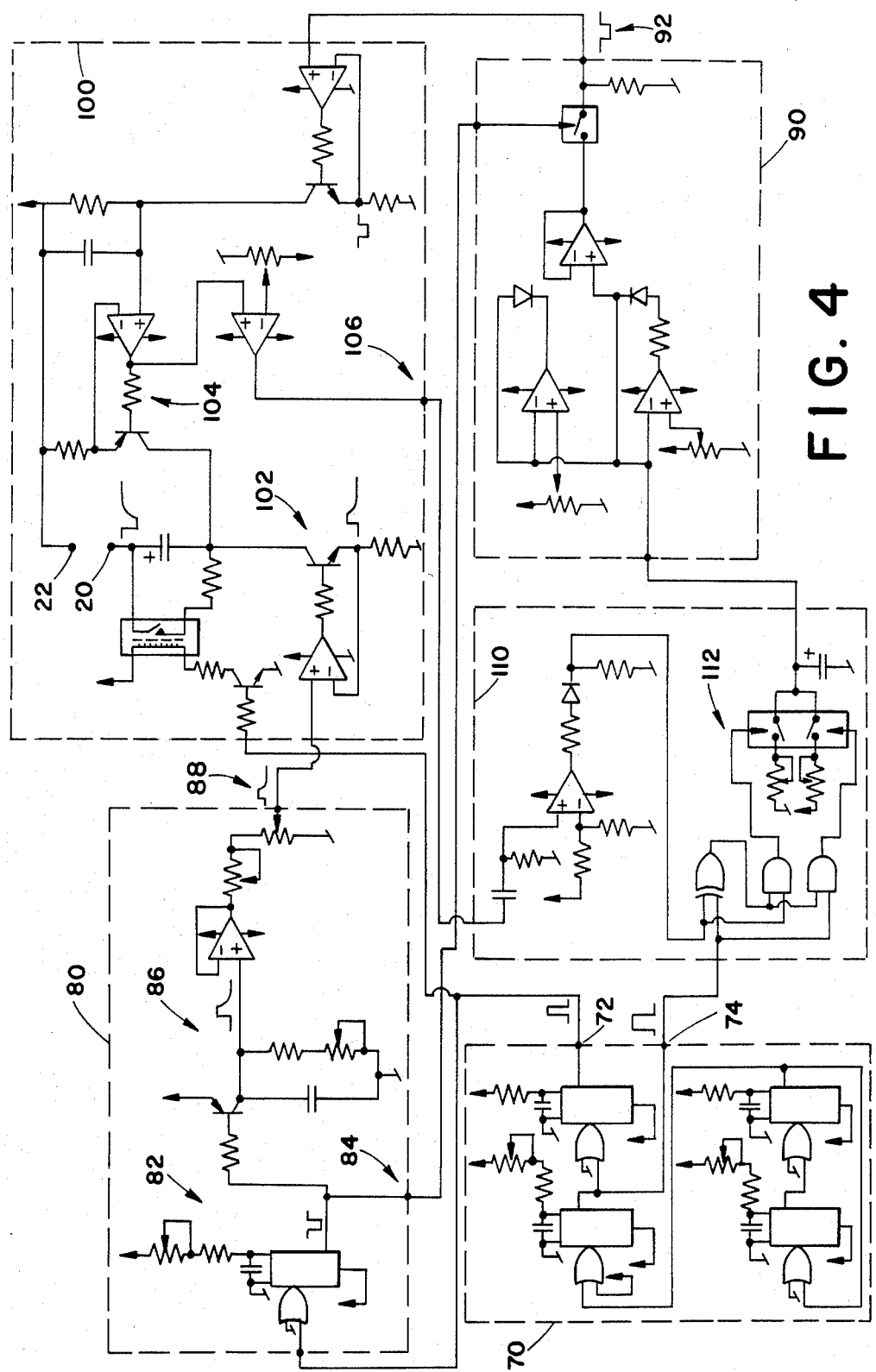

With reference to FIG. 4, the signal generator C cyclically generates the current wave form illustrated in FIG. 3 across the electrodes. A timebase circuit 70 periodically generates synchronizing output signals 72 and 74. A synchronizing pulse from the timebase circuit output 72 triggers a shaping circuit 80. The shaping circuit 80 includes a pulse width generating portion 82 for defining the plateau phase 54 and producing a synchronizing pulse at output 84. An exponential decay generating portion 86 defines an exponentially decaying trailing edge 56 from the plateau phase 54. The exponentially decaying, trailing edge defined by circuit 86 exponentially approaches zero magnitude. The combined plateau and trailing edge signals define a primary pulse phase at an output 88.

A reverse current clamping circuit 90 under the synchronization of a synchronizing pulse from the output 84 of the primary pulse shaping circuit 80 generates a voltage wave form 92. An output stage 100 receives the voltage wave forms from the shaping circuit 80 and the reverse current clamping circuit 90. The primary pulse phase 88 from the shaping circuit 80 drives a first voltage to current converter 102 and the reverse polarity pulse 92 from the clamping circuit 90 drives a second voltage to current converter 104. The first and second voltage to current converters generate currents of opposite polarity across the electrodes 20, 22 to generate a current wave form of the configuration of FIG. 3.

A reverse current minimizing circuit 110 receives both a synchronizing pulse from output 74 of the timebase circuit 70 and a feedback signal 106 from the output stage 100 to control a reverse polarity pulse amplitude controlling circuit 112 which self-adjusts the reverse current level to a minimum. In this manner, the signal generating circuit C generates the biphasic balanced wave form.

The invention has been described with reference to the preferred embodiments. Obviously, modifications and alterations will occur to others upon reading and understanding the preceding detailed description of the preferred embodiments. It is intended that the invention be construed as including all such alterations and modifications insofar as they come within the scope of the appended claims or the equivalents thereof.

Having thus described a preferred embodiment of the invention, the invention is now claimed to be:

1. A method of generating an antidromic action potential traveling unidirectionally along a nerve trunk while maintaining a balanced net charge transfer therealong, the method comprising:

applying an electrical waveform including a first current pulse portion of a first polarity and a second current pulse portion of a second polarity to the nerve trunk, the first current pulse portion including:
a rapid amplitude increasing portion,
a relatively stable amplitude plateau portion, and
a discontinuity free decreasing portion;
the second pulse portion including:
an opposite polarity increasing portion which follows the first pulse portion with a smoothly and transition-free interface therebetween, the opposite polarity pulse portion having a relatively small amplitude as compared to the first pulse portion and a relatively long duration as compared to the first pulse portion;
the first pulse portion decreasing portion and the second polarity increasing portion taken together form a smooth, continuous waveform portion whose first derivative is smooth and continuous from the plateau portion through the interface to the opposite pulse relatively small amplitude.

2. The method as set forth in claim 1 wherein the charge transfer during the first pulse portion is substantially equal and opposite to the charge transfer during the second pulse portion.

3. The method as set forth in claim 2 wherein the second pulse portion includes a constant amplitude portion.

4. The method as set forth in claim 3 wherein the first polarity pulse portion increases rapidly to a trigger amplitude in the range of ½ to 20 milliamps.

5. The method as set forth in claim 3 wherein the first pulse portion plateau portion has a duration of 100 to 3000 microseconds.

6. The method as set forth in claim 3 wherein the first pulse portion plateau portion lasts about 1 to 10% of the cycle duration.

7. The method as set forth in claim 3 wherein the first pulse portion decreasing portion and the second pulse portion increase portion together have a duration in the range of 100 to 3000 microseconds.

8. The method as set forth in claim 3 wherein the first and second pulse portions are applied cyclically at a rate between 1 and 100 hertz.

9. An apparatus for causing the generation of antidromic action potentials, the apparatus comprising:
a cathode electrode dimensioned for substantially encircling a nerve trunk;
an anode electrode configured to be disposed in an electrically conductive relationship with the cathode electrode through the body fluids and the nerve trunk; and,
a signal generator for cyclically generating a train of biphasic current pulses which includes alternating first polarity pulse portions and second, opposite polarity pulse portions, the first polarity pulse portions having a sharp leading edge and an amplitude great enough to trigger antidromic action potentials, each first pulse portion having a decaying trailing edge which diminishes smoothly and without discontinuities such that a first-derivative thereof increases smoothly and continuously, each second pulse portion having a leading edge which is smooth and continuous with the first pulse trailing edge without discontinuities at an interface therebetween such that the first derivative is smooth and continuous across the interface, each second pulse portion having an amplitude less than the trigger amplitude to avoid triggering action potentials in an opposite direction along the nerve trunk, the second pulse portion terminating generally at the first pulse portion leading edge of the next cycle.

10. The apparatus as set forth in claim 9 wherein the cathode electrode is an annular ring.

11. The apparatus as set forth in claim 9 wherein the cathode electrode is disposed in an interior bore of a dielectric sleeve, which dielectric sleeve is adapted to be disposed circumferentially around the nerve trunk.

12. The apparatus as set forth in claim 11 wherein the cathode electrode is disposed asymmetrically within the dielectric sleeve.

13. The apparatus as set forth in claim 12 wherein the anode electrode is adapted to be disposed in body fluids displaced from the dielectric sleeve.

14. The apparatus as set forth in claim 9 wherein the signal generator includes:
   a primary pulse shaping circuit for generating a monophasic primary pulse which has a square wave portion and an exponential decay portion;
   a reverse current clamping circuit for generating a monophasic reverse polarity phase; and,
   an output circuit for combining the primary and reverse polarity pulses and applying the current pulses across the cathode and anode.

15. The apparatus as set forth in claim 14 wherein the signal generator further includes a reverse current minimizing circuit for controlling the amplitude of the reverse polarity pulse such that the charge transfer during the second pulse portions substantially equals the charge transfer during the first pulse portions, the reverse current minimizing circuit being operatively connected with the output circuit for receiving a feedback portion of the biphasic pulses.

16. A method of generating an antidromic action potential traveling along a nerve trunk while maintaining a balanced net charged transfer therealong, the method comprising:
   applying a first polarity rapidly increasing amplitude current to the nerve trunk, the current amplitude increasing sufficiently to trigger antidromic action potentials along the nerve trunk;
   maintaining the applied current relatively stable at a first amplitude;
   exponentially decreasing the applied current until current of an opposite polarity and a second amplitude is being applied, the exponential current decrease and the slope thereof being smooth and discontinuity-free such that the exponential decreasing current is free of sudden current amplitude changes which may trigger an action potential traveling along the nerve trunk, the second amplitude being smaller in magnitude than the first amplitude; and,
   continuing to apply current of the second polarity and generally the second amplitude until the net charge transfer along the nerve is balanced.

17. A method of generating an antidromic action potential traveling unidirectionally along a nerve trunk while maintaining a balanced net charge transfer therealong the method comprising:
   cyclically applying an electrical waveform each cycle of which includes:
   a rapid amplitude increasing portion,
   a relatively stable first polarity plateau connected with the rapid amplitude increasing portion,
   a relatively stable second polarity plateau, the second plateau having a relatively small magnitude and a relatively long duration as compared to the first polarity plateau, and
   a smooth, discontinuity-free transition portion connected with the first and second polarity plateau, the slope of the transition portion being smooth and discontinuity-free between the first and second polarity plateaus.

* * * * *